United States Patent [19]

Wretlind et al.

[11] Patent Number: 4,917,880
[45] Date of Patent: Apr. 17, 1990

[54] IODINE-CONTAINING EMULSION

[75] Inventors: Karl A. J. Wretlind, Stockholm; Bengt M. Ajaxon, Upsala, both of Sweden

[73] Assignee: Kabivitrum AB, Stockholm, Sweden

[21] Appl. No.: 204,718

[22] Filed: Jun. 10, 1988

[30] Foreign Application Priority Data

Jun. 11, 1987 [EP] European Pat. Off. ........ 87850192.3

[51] Int. Cl.⁴ .............................................. A61K 49/04
[52] U.S. Cl. ........................................................ 424/5
[58] Field of Search ............................................ 424/5

[56] References Cited

U.S. PATENT DOCUMENTS 4,404,182 9/1983 Vermess et al. ........................ 424/5

FOREIGN PATENT DOCUMENTS 58-32829 2/1983 Japan ....................................... 424/5
676738 7/1952 United Kingdom ..................... 424/5

Primary Examiner—Frederick E. Waddell
Attorney, Agent, or Firm—Pollock, Vande Sande & Priddy

[57] ABSTRACT

The invention relates to an emulsion for use as an X-ray contrast agent and containing one or more iodinated lipids emulsified in an aqueous phase. The emulsion contains one or more amino acids, fatty acids or their salts, fat-soluble vitamins and/or urea for increasing its stability. Furthermore, the emulsion may contain one or more pharmacologically acceptable oils or fats.

By the stability-increasing agent, it has been possible to prepare emulsions of iodinated lipids which can be sterilized in an autoclave and be stored for a long time without the emulsion breaking.

11 Claims, No Drawings

IODINE-CONTAINING EMULSION

A great number of iodine-containing compounds are used as contrast agents in X-ray practice. One of these is iodinated fat. the iodinated fat has for a long time turned out to be of great value in X-ray work, i.e. for examining lymphatic vessels, bronchi and other body cavities. However, the iodinated fat as such cannot be administered intravenously, as it would then give rise to fat embolisms in lungs and other organs. Consequently, the possibilities of formulating compositions containing the iodinated fat in such a form that it might be administered intravenously have been investigated in several connections. A fat emulsion is then the only form of preparation that may be considered for intravenous administration. Such emulsions with iodinated fat have also been prepared. These iodine-containing fat emulsions have been found to have certain advantages. Thus, they are i.e. characterized by a low osmotic pressure. On the other hand, the X-ray opacity has not been sufficient in order that they might be used in ordinary X-ray examinations of blood vessels.

Iodine-containing fatty emulsions have attracted a special interest due to the uptake by the cells of the reticuloendothelial system (RES cells). This observation was made as early as 1930 by W S Keith, D R Briggs (Proc. Soc. Exp. Biol. Med. 27: 538, 1930). Through this, the liver and the spleen, having a great number of RES cells, can be made more opaque to X-rays. However, it has only in recent years become possible to utilize this quality of iodine-containing emulsions, as more sensitive methods for X-ray examination by means of computer tomography have been developed. Accordingly, there has appeared a possibility of making more accurate X-ray examinations than before of the liver, for example. An examination of the liver in this way might also mean that small tumors, metastases, abscesses, etc. in this organ might be observed more easily than before. One of the explanations of this is that the RES cells, which have so far been considered to take up the emulsion, are not present in tumors. Thus, as the tumors do not take up contrast agents, they can be observed as "recesses" in the image obtained by computer tomography. In view of the great possibilities here indicated for an improved X-ray diagnosis, various methods of preparing iodine-containing fat emulsions for intravenous use have been examined intensively over the years.

In the following, a summary is given of previous publications as well as patents and patent applications concerning iodine-containing fat emulsions for X-ray examination of the liver and spleen.

1. Roth, Stephan. "Röntgenkontrastmittel auf der Basis einer Emulsion von jodierten Ölen". Patent specification DE 26 02 907 (1976-01-27).

The invention relates to an emulsion (oil in water) containing iodinated triglyceride and characterized in that it contains 50-60% of an iodinated triglyceride and 2-10% of a polyoxyethylene-sorbitan fatty acid ester as an emulsifier. The resulting emulsion could only be sterilized by means of gamma rays. The emulsion is intended for use in lymphoangiography and hepatosplenography.

2. Grimes, George and co-workers. "Formulation and Evaluation of ethiodinated oil Emulsion for intravenous Hepatography". Journal of Pharmaceutical Sciences 68: 52-56, 1979.

The authors prepared various emulsions with iodinated oil and studied the effects of these in rabbits and monkeys. The possibility of making sterile emulsions was examined in this connection. It was not possible to carry out heat sterilization by autoclaving. Accordingly, a method was developed comprising sterile filtration of the oil ("ethiodized oil") and of the water solution of the used emulsifiers separately, after which the homogenization was carried out aseptically. The examined emulsifiers were polysorbate 80, sorbitan monooleate and phosphatidyl choline. According to the authors, the emulsions considered to be suitable as contrast agents for the liver should have a particle size of 2-3 $\mu$m in diameter. If the average particle size was less than 0.75 $\mu$m in diameter, the emulsion was not considered to be useful as a contrast medium.

3. Vermess, Michael et al. "Development and experimental evaluation of a contrast medium for computed tomographic examination of the liver and spleen". J. Comput. Assist. Tomogr. 3: 25-31, 1979.

The authors describe several iodine-containing fat emulsions having a varying composition. The emulsion that was considered to be the best one was called EOE 13 and contained 53% v/v of Ethiodol, 10% of alcohol, 0.45% of soy lecithin and a phosphate buffer adjusted to pH 7. About 55% of the oil was present as particles having a diameter of 1-3 $\mu$m. These authors maintained that the size of the particles must be within the range from 2 to 4 $\mu$m in order to obtain a sufficient absorbtion in the liver by the emulsions used.

4. Vermess, Michael et al. "Ethiodized oil Emulsion for intravenous Hepatography". U.S. Pat. No. 4 404 182, 1983-09-13.

This patent relates to preparation of iodinated fat emulsions with lecithin as emulsifier. According to the patent, the emulsion should be prepared in such a way that 30-35% by volume of the fat particles have a diameter of 2-3 $\mu$m. The emulsion is sterilized by filtration, as it does not resist heat sterilization (autoclaving). The emulsion is intended for use in animals, preferably rabbits and monkeys.

5. Schumacher, K A et al, Europ. J. Radiol. 5: 167-174, 1985, report tests with a great number of different emulsions containing iodinated fat. The emulsions were prepared with many different emulsifiers such as polyoxyethylene-;b 4-sorbitan monolaurate, Hydrophilic Lipophilic Balance (HLB) 12,1 (Tween ® 21, Atlas Chemie), polyoxyethylen-20-sorbitan monooleate, HLB 15.3 (Tween ® 80, Serva), glycerol polyethylene glycol ricinoleate, HLB 14.5 (Cremophor ® EL), dicetylphosphate DP (Sigma), lecithin from egg (Fluka GmbH), oxypolygelatine (Gelinfundol ® 5.5%, Biotest GmbH) and dextran 60 (Macrodex ® 4.5% RL Knoll).

Lipomicrons were prepared with a varying droplet size of the iodinated fat and said emulsifiers. The resulting emulsions (lipomicrons) were destroyed in heat sterilization. For this reason they were kept sterile by addition of "P.S.N. antibiotic mixture". Several of the prepared emulsions caused a blood pressure decrease at intravenous injection on rats and dogs. Tests showed that the various lipomicrons were absorbed in the liver and spleen to a varying degree, i.a. depending on the size of the fat particles.

6. Reinig, James et al. (Radiology 162: 43-47, 1987) have used the emulsion EOE-13 for visualizing the liver by means of computer tomography. They state that the particle size in the emulsion used was 1-4 $\mu$m. The emulsion EOE-13 is prepared from iodinated ester of fatty acids from poppyseed oil. In liver examinations an amount of 0.25 ml/kg was administered in the course of one hour. The authors stated that EOE-13 was an unstable emulsion and was difficult to prepare in large quantities. Moreover, EOE-13 caused side effects (fever and cold flushes), resulting in that the patients had to be pretreated with steroids.

7. Farbenfabriken Bayer, G. B. patent 676 738, describes an emulsion with iodinated oil or iodinated fatty acid esters and with synthetic nonionactive emulsifiers. In order to counteract side effects, thiosulfate is added to the preparation. The compositions must be heated to 37° C. before injection, as they are semi-solid at room temperature. Nothing is said about stability at heat sterilization of the preparation.

8. Astra, GB patent 721 264

This patent relates to preparations of an X-ray contrast agent dissolved or dispersed in water to which a viscosity increasing agent has been added so that the ratio of the "dynamic viscosity" of the preparation to its density, i.e. the "kinematic viscosity", is of the same order as for blood which should give flow properties similar to blood. Nothing is said about sterilization methods. The collection of examples includes various iodinated substances and thickeners. In example 6, for example, an ethyl ester of di-iodostearic acid+-polyvinylpyrrolidone is used and as an emulsifier polyoxyethylene sorbitan monooleate.

9. Merck, DE patent 501 876 and the corresponding FR 681 095.

These two patents describe the use of esters of alcohols (having up to 8 C atoms) with higher fatty acids. Because of their lower viscosity these esters can be better distributed than previously used iodinated fats which are highly viscous.

10. Leo, U.S. Pat. No. 3 358 575 and the corresponding GB patent 1 070 517.

These patents relate to an autosterile X-ray contrast agent containing iodinated vegetable oil or iodinated ester of vegetable oil in the form of an anhydrous emulsion with glycerol and lecithin. The preparation is a concentrate which must be diluted with sterile water before injection. It is apparent from the text that a concentrate has been chosen because after dilution with water, aggregation of the particles and hydrolysis of the fat with formation of free fatty acids and iodide takes place at storage of the ready-to-use emulsion. This means that the emulsion must be used immediately after its preparation. Another reason for the choice of a concentrate is that heat sterilization of the diluted ready-to-use emulsion has been found not to be possible without the emulsion being broken.

It is apparent from example 8 that the diluted emulsion contains 18% of glycerol and 18% of oil. The glycerol content is 8 times higher than for a glycerol solution isotonic with blood.

11. Guerbet, FR 1 005 875.

This patent refers to iodinated ethyl esters of fatty acids from poppyseed oil (Lipiodol Ultra Fluid). Because of its lower viscosity it could be removed more easily, e.g. from the spinal channel than the iodinated poppyseed oil (Lipiodol) so far used. By mixture with a non-iodinated oil a suitable density could be obtained. However, this patent does not relate to an emulsion.

The emulsions mentioned above with iodinated fat have several disadvantages. Thus, it has not been possible (1) to prepare emulsions having a particle size of less than 0.5 μm, which is required for the emulsion to be stable
(2) to prepare emulsions that are stable after heat sterilization by autoclaving
(3) to obtain a satisfactory stability in long-time storage
(4) to attain the required tolerance, i.a. depending on the use of synthetic emulsifiers, such as Tween ® and Span ® etc.

12. In a publication by Thomas, S. F. and co-workers (Hepatoliengraphy: Past, Present and Future, Radiology 57: 669–684, 1951) those properties are reported which are required from an X-ray contrast agent to visualize the liver and spleen. According to the authors, such a contrast agent should 1. have little or no acute or chronic toxicity
2. not be radioactive
3. contain an element having an atomic number high enough to give a sufficient X-ray opacity also when administered in moderate quantities
4. be possible to administer intravenously without difficulties
5. have a high affinity to selective absorbtion in the liver and spleen.
6. be excreted rapidly and safely from the body.

The authors finish the enumeration of desirable properties stated above with the following sentence: "It seems unlikely that a single medium fulfilling all of these criteria can be obtained".

However, by the present invention, it has been possible to eliminate the indicated disadvantages and prepare iodine-containing fat emulsions meeting the demands mentioned above.

Thus, it is apparent from the previous publications, patents and patent applications that it has not been possible to prepare an intravenous iodine-containing fat emulsion which is clinically useful. None of the previously prepared emulsions has the properties required, viz. stable in heat sterilization, stable in long-time storage, a particle size below 0.5 μm and required tolerance at intravenous administration. However, after lengthy investigation we have found a method, by which it is possible to prepare such an iodine-containing emulsion with the desired properties. The invention is based on the fact that a fat emulsion containing organically bound iodine can be produced by means of suitable additives and preferably the use of egg yolk phospholipids as emulsifiers, said fat emulsion exhibiting a good stability both in autoclaving and longtime storage as well as a good tolerance at intravenous administration. An emulsion prepared according to this invention has also the quality that it is absorbed, i.e. in the liver and the spleen. Thus, it can be used in X-ray examinations, such as computer tomographic examinations, in order to diagnose tumors, etc. in the liver, spleen and other organs. Quite surprisingly, it has also been found that emulsions according to the invention remain in the circulation of the blood for such a long time that there will be time for carrying out the desired examinations of blood vessels and heart by means of computer tomography.

When an iodine-containing fat is emulsified by means of an emulsifier, such as egg yolk phospholipid, an emulsion is obtained which does not resist autoclaving. In this heat treatment the emulsion is broken and becomes unusable. As according to this invention an oil is used instead in the preparation of the emulsion, which oil consists of a mixture of 10-30% by volume of iodinated fat (triglyceride or another ester of fatty acids) and 70-90% by volume of soybean oil or another pharmacologically acceptable oil as well as egg yolk phospholipid as emulsifier, an emulsion can be obtained which has a particle size of less than 0.5 μm with a good stability after autoclaving and a high tolerance at intravenous administration.

However, an addition of a non-iodinated oil has the effect that the X-ray opacity of the emulsion becomes low. Moreover, unnecessarily great amounts of fat will be provided in X-ray diagnostic examinations. However, there are situations where the use of such an iodine-containing fat emulsion having a low X-ray opacity and a good tolerance can be of value.

In tests it has quite surprisingly been found that stable emulsions of iodinated fatty acid esters can be obtained without the mentioned addition of soybean oil or another oil, if the emulsion instead as a stability-increasing agent contains certain organic compounds, such as amino acids, fatty acids or their salts, fat-soluble vitamins and/or urea. In this way it will be possible to obtain emulsions of iodinated fatty acid esters having a very good stability in autoclaving and storage. These emulsions have also a higher X-ray opacity than emulsions to which a non-iodinated oil (triglyceride) has been added.

Thus, the present invention refers to emulsions for parenteral, especially intravenous, administration and containing one or more iodine-containing lipids, such as triglycerides or alkyl esters of fatty acids, optionally one or more pharmacologically acceptable oils or fats and as a stability-increasing agent one or more amino acids, fatty acids or their salts, fat-soluble vitamins and/or urea. The particles of the emulsion preferably have a size of less than 0.5 μm.

Examples of those organic compounds that can be included in the emulsions of the invention to increase their stability are amino acids, such as phenylalanine, alanine, leucine, isoleucine, glycine, serine and taurine. This enumeration does not exclude the use of other amino acids having a similar effect.

Organic fatty acids preferably contain from 8 to 22 carbon atoms in their molecule and can, for instance, consist of pelargonic acid, oleic acid or linoleic acid. Instead of the free acids, their salts, for example with alkali metals, can also be used. An example of a fat-soluble vitamin is vitamin E. As stated above, urea has also been found to be a suitable additive.

The stability-increasing compounds are usually included in the emulsion in a concentration of from 0.1 to 5% by weight, calculated on the final emulsion.

Instead of soybean oil, which is pharmacologically acceptable, any fat or oil of a vegetable or animal origin can be used which without objections can be included in compositions to be administered parenterally, especially intravenously. Thus, besides soybean oil, safflower oil, cottonseed oil, peanut oil and fish oils, for example, can be used. Other oils and fats can also be used, as is well-known to one skilled in the art. The oil or fat can be included in the emulsion in an amount up to 50% by volume of the emulsion. Instead of or together with the pharmacologically acceptable oil or fat, triglycerides of a similar composition and prepared in a completely or partially synthetic way, can be included.

The iodine-containing lipid can consist of any one of the iodinated lipides previously known for use as X-ray opaque agents. Such lipids are usually iodinated fatty acids in the form of glycerol or alkyl esters. As is shown in the report on the state of art, several of them are previously known to those skilled in the art. According to the invention, iodinated triglycerides or fatty acids are preferably used, which optionally can be used after iodinating in the form of esters such as methyl, ethyl or glycerol esters. These triglycerides or fatty acids can be derived from poppyseed oil, soybean oil, peanut oil, cottonseed oil, safflower oil, sunflower oil, menhaden oil, salmon oil, herring oil or other vegetable or animal oils. Esters of pure fatty acids can also be used. Examples of such ones are the ethyl or methyl ester of triiodostearic acid. Esters of other fatty acids that can be iodinated are also suitable, provided a sufficient X-ray opacity can be attained. This enumeration of various iodized lipides is not restricting.

The iodinated fatty acids in the form of esters, such as methyl, ethyl or glycerol esters, are usually included in the emulsion in an amount of from 2.5 to 65% by volume and preferably 2.5 to 40% by volume. At lower concentrations, a sufficient X-ray opacity is usually not attained, while at higher concentrations difficulties may arise in preparing a sufficiently stable emulsion.

The preparation of the iodine-containing lipids has been known for a long time to those skilled in the art and need not be described here in more detail. Such preparation is, for instance, described in US-A 1 840 034, US-A 1 870 023 and EP-A 1 198 344.

The emulsion of the invention also contains one or more emulsifiers. Such emulsifiers must be pharmacologically acceptable and must not create any side effects at the administration. A plurality of such emulsifiers have been known to those skilled in the art for a long time for use in fat emulsions to be administered intravenously and the most known and preferred ones, according to the invention, are natural phospholipids or phosphatids from egg yolk. These phospholipids have been found to give a good emulsifying effect and a very slight frequency of side effects, provided that they are isolated and prepared in a pharmacologically unobjectionable way. Pharmacologically inactive fractions of soybean phospholipids can also be used. Additions of other emulsifiers ("co-emulsifiers") can possibly also be included, such as acetylated monoglycerides or sorbitan esters of long-chain fatty acids.

Moreover, the emulsion usually contains other auxiliary substances known per se, such as for adjusting the isotonicity, preservatives, pH-adjusting agents, etc. Such auxiliary substances are well-known to those skilled in the art and need not be described here in detail.

The emulsions are prepared in a conventional manner. The iodinated fat and the optionally used additional fat or oil are mixed with the aqueous phase, the emulsifiers and auxiliary substances used and the stability-increasing compound or compounds, after which all this is homogenized to the desired particle size. For an emulsion to be injected into the blood vessels, all particles must have a size less than that of the blood corpuscles of about 8 μm and, as stated above, the particles in the present emulsion should have a size of less than 0.5 μm. To adjust a suitable particle size of the emulsion is no problem for one skilled in the art, when the constituents of the emulsion are those intended in this invention.

It is important that the components used are of a pharmacologically faultless quality from the start and that this quality is maintained throughout the production process of the individual components and the solution. Thus, particularly the fat materials and phospholipids used should be carefully purified, for example by means of suitable extraction and precipitation methods, and htey should be protected in storage and production from contact with oxygen, so that no oxidation products are formed. Preparation of pharmacologically unobjectionable phospholipid and oil is for instance described in U.S. Pat. No. 3 169 094. An inert atmosphere, for instance nitrogen gas, should also be used when preparing and bottling the emulsion of the invention.

The emulsions of the invention are primarily intended for intravenous administration. However, they are not restricted to merely this way of administration but every type of parenteral administration to different body cavities is possible. Those modifications of the composition of the emulsion which are conditioned by different ways of administration are well-known to those skilled in the art.

The invention is illustrated in more detail in the following examples.

EXAMPLE 1

| Ethiodized Oil Injection USP XXI | 10 ml |
| Phenylalanine | 0.1 g |
| Phospholipid from egg | 1.2 g |
| Glycerol | 2.25 g |
| Sterile water | to 100 ml |

After homogenization and a subsequent autoclaving at 121° C. the emulsion was shake tested. The average particle size was 0.24 μm after shaking for 48 hours. This shows that the emulsion was stable after heat sterilization and also after shake testing. Repeated freezing could not break the emulsion, which further shows its good stability.

The "Ethodized Oil Injection USP XXI" used in this example and the following examples is an addition product of iodine to the ethyl ester of the fatty acids from poppyseed oil. It contains at least 35.2 and maximum 38.9% of organically bound iodine and is sterile.

EXAMPLE 2

| Ethiodized Oil Injection USP XXI | 2.5 ml |
| Leucine | 0.1 g |
| Soybean oil | 7.5 ml |
| Phospholipid from egg | 1.2 g |
| Glycerol | 2.25 g |
| Sterile Water | to 100 ml |

After homogenization and a subsequent autoclaving at 121° C. the emulsion was shake tested. The average particle size was 0.26 μm after shaking for 48 hours, which shows that the emulsion had a satisfactory stability.

EXAMPLE 3

An emulsion was prepared in the same way as in example 1, with the exception that iodinated soybean oil was used instead of Ethiodized Oil Injection USP XXI. This emulsion had an average particle size of 0.24 μm and in other respects the desired properties.

EXAMPLE 4

An emulsion prepared in accordance with example 1 was examined in respect of tolerance at intravenous administration to rats. It was intended to find the dose tolerated by rats at a continuous infusion at a rate of 0.6 ml/kg/min. The iodine-containing emulsion was infused via a central vein catheter, which had been inserted by operation a few days before the test. During the test the animals were in metabolism cages and could move freely. The infusion rate was kept constant by means of an infusion pump. The device used was the same as reported in the article "Growth and nitrogen Utilization in Rats on continuous and intermittent parenteral Nutrition with and without Fat (Intralipid 20%)" by K-A Roos, S. Meurling and G. Sandberg, Acta Chir. Scand. 147: 459-464, 1981. The infusions could go on for 6 hours without the animals dying. As it was also intended by the test to study the distribution of the fat emulsion in the body, the animals were killed by injection with Hypnorm ® (injection solution containing fluonison and phentanyl citrate) immediately after the infusions. This test shows, that tolerance corresponds to 150–200 ml/kg in rats, which is more than twice the blood volume. The tolerance must therefore be regarded as satisfactory.

EXAMPLE 5

This test was carried out to find the doses tolerated at bolus injection (one-shot injection) of the iodine-containing emulsion according to example 1 to rats. The preparation was injected in four different doses of 0.6, 2.4, 7.2 and 21.6 ml/kg within 10 and 30, 30 and 40 seconds, respectively. The injections were made via a central vein catheter, which had been inserted by operation a few days earlier. The animals behaved quite normally during and after the injections. During the 120 hours, when the animals were observed after the injections, no influence whatsoever could be observed. After this time the animals were killed in order that the presence of iodine in different organs might be examined.

The results of the test show that rats tolerate more than 21.6 ml of iodine-containing emulsion according to example 1 per kg body weight at bolus injection. These amounts considerably exceed the quantities of emulsions calculated to be used in X-ray examinations. Thus, the test verifies the high tolerance to the emulsion according to the invention.

EXAMPLE 6

It was intended by this test to examine the secretion of iodine via urine and feces after supply of iodine emulsion according to example 1.

Three male rats were used for the test. The emulsion was infused via a catheter by means of an infusion pump so that each animal obtained a dose of 20 ml/kg at a rate of 20 ml/h.

Urine and feces were collected quantitatively every 24th hour for four consecutive days and analyzed as to their content of iodine.

All the animals tolerated the infusions well without observable trouble. The iodine content of the feces was low and constituted only 1-3% of the excreted quantity per 24 h. After 24 hours about 40% of the amount supplied had been excreted and after 96 hours 80% of the supplied amount of iodine had disappeared from the body.

The test showed that iodine after infusion of 848 mg/kg in the form of iodine emulsion was eliminated without complications, substantially via the urinary tract, and that the elimination process follows the kinetics of the first order.

EXAMPLE 7

| Ethiodized Oil Injection USP XXI | 20 ml |
|---|---|
| Phenylalanine | 0.2 g |
| Phospholipid from egg | 2.0 g |
| Myvacet ® (acetylated monoglycerides) | 1.0 g |
| Glycerol | 5 g |
| Sterile water | to 100 ml |

After homogenization of the constituents and a subsequent autoclaving at 121° C. the particle size of the emulsion was determined in a Coulter Nanosizer to be 0.25 μm. The content of iodine in a determination according to USP XXI was 9.7 g of iodine per 100 ml.

EXAMPLE 8

| Ethiodized Oil Injection USP XXI | 15 ml |
|---|---|
| Alanine | 0.15 g |
| Phospholipid from egg | 1.7 g |
| Glycerol | 5 g |
| Sterile water | to 100 ml |

The mixture was homogenized and heat sterilized at 121° C. after filling in injection flasks under protection with nitrogen gas.

EXAMPLE 9

| Iodized soybean oil | 10 ml |
|---|---|
| Phenylalanine | 0.25 g |
| Phospholipid from egg | 1.2 g |
| Glycerol | 2.25 g |
| Sterile water | to 100 ml |

After homogenization of the mixture, bottling and a subsequent autoclaving at 121° C., the average particle size was determined to be 0.24 μm. The emulsion was stored alternatingly in a refrigerator and at room temperature (2 days each time) for 24 days without any change of the particle size appearing.

EXAMPLE 10

| Iodized soybean oil | 2.5 ml |
|---|---|
| Phenylalanine | 0.1 g |
| Soybean oil | 7.5 g |
| Phospholipide from egg | 1.2 g |
| Glycerol | 2.25 g |
| Sterile water | to 100 ml |

After homogenization of the mixture, bottling and a subsequent autoclaving at 121° C., the average particle size was determined to be 0.22 μm. After alternating storage in a refrigerator and at room temperature (2 days each time) for 24 days, the particle size was again determined. No change had occurred.

We claim:

1. Emulsion for use as an x-ray contrast agent which is stable to heat sterilization and during long-term storage and which contains at least one iodinated lipid selected from the group consisting of iodine-containing triglycerides and iodine-containing alkyl esters of fatty acids, which are emulsified in an aqueous phase by means of at least one emulsifier selected from the group consisting of egg yolk phospholipids and soybean phospholipids and wherein said emulsion further contains, as a stability-increasing agent, at least one member selected from the group consisting of amino acids and urea, and further, optionally, also one or more pharmacologically acceptable oils or fats, and wherein the lipid particles of the emulsion have a size of below 0.5 μm.

2. The emulsion of claim 1 wherein the iodinated lipid is included in an amount of from 2.5 to 40 volume percent.

3. The emulsion of claim 1 which further includes an isotonic agent.

4. The emulsion of claim 3 wherein said isotonic agent includes glycerol.

5. Emulsion as claimed in claim 1, characterized in that the stability-increasing agent is included in an amount of totally from 0.1 to 5 weight percent, based on the final emulsion.

6. Emulsion as claimed in claim 1, characterized in that the iodinated lipid is included in an amount of from 2.5 to 65 volume percent.

7. Emulsion as claimed in claim 1, characterized in that the pharmacologically acceptable oil(s) or fat(s) is (are) included in an amount of up to 50 volume percent.

8. Emulsion as claimed in claim 1, characterized in that the total amount of fat material consists of from 10 to 30 volume percent of iodinated lipid or lipids and from 90 to 70 volume percent of pharmacologically acceptable oil or fat.

9. Emulsion as claimed in claim 1, characterized in that the stability-increasing agent is selected among phenylalanine, alanine, isoleucine, leucine, glycine, serine, taurine, and/or urea.

10. Emulsion as claimed in claim 1, characterized in that the pharmacologically acceptable oil or fat consists of soybean oil, cottonseed oil, peanut oil and/or fish oils.

11. Emulsion as claimed in claim 1, characterized in that the iodinated lipid or lipids is selected among esters of iodinated fatty acids derived from poppyseed oil, cottonseed oil, soybean oil, peanut oil, safflower oil, sunflower oil, menhaden oil, salmon oil, herring oil or other vegetable or animal oils and/or esters of iodinated stearic acid, oleic acid, linoleic acid or other fatty acids.

* * * * *